United States Patent
McGee

(10) Patent No.: US 12,036,530 B2
(45) Date of Patent: Jul. 16, 2024

(54) GAS TREATMENT METHOD AND MATERIALS

(71) Applicant: Hamilton Sundstrand Corporation, Charlotte, NC (US)

(72) Inventor: Randolph Carlton McGee, Hamden, CT (US)

(73) Assignee: HAMILTON SUNDSTRAND CORPORATION, Charlotte, NC (US)

(*) Notice: Subject to any disclaimer, the term of this patent is extended or adjusted under 35 U.S.C. 154(b) by 0 days.

(21) Appl. No.: 18/168,105

(22) Filed: Feb. 13, 2023

(65) Prior Publication Data

US 2023/0182117 A1 Jun. 15, 2023

Related U.S. Application Data

(62) Division of application No. 15/968,691, filed on May 1, 2018, now Pat. No. 11,577,224.

(51) Int. Cl.
*B01J 21/06* (2006.01)
*B01D 53/00* (2006.01)
(Continued)

(52) U.S. Cl.
CPC .......... *B01J 21/063* (2013.01); *B01D 53/007* (2013.01); *B01D 53/8687* (2013.01); *B01J 8/1827* (2013.01); *B01J 27/24* (2013.01); *B01J 35/39* (2024.01); *B01J 35/50* (2024.01); *B01J 37/0209* (2013.01); *B01D 2255/20707* (2013.01); *B01D 2255/707* (2013.01); *B01D 2255/802* (2013.01);
(Continued)

(58) Field of Classification Search
CPC ..... B01D 53/885; B01J 21/063; B01J 35/004; B01J 21/06
See application file for complete search history.

(56) References Cited

U.S. PATENT DOCUMENTS

| | | | |
|---|---|---|---|
| 4,287,156 A | 9/1981 | De Feo | |
| 4,374,663 A | 2/1983 | Collin et al. | |

(Continued)

FOREIGN PATENT DOCUMENTS

| | | |
|---|---|---|
| CN | 1557550 A | 12/2004 |
| CN | 1712128 A | 12/2005 |

(Continued)

OTHER PUBLICATIONS

European Office Action for European Application No. 19172141.4; Application Filing Date: May 1, 2019; Date of Action: Apr. 9, 2021; 5 pages.

(Continued)

*Primary Examiner* — Nicholas A Smith
(74) *Attorney, Agent, or Firm* — CANTOR COLBURN LLP

(57) ABSTRACT

A method is disclosed in which a gas of hydrogen and nitrogen, or hydrogen and ammonia, or hydrogen, nitrogen, and ammonia, is introduced to a fluidized bed. The gas flows through the fluidized bed, and titanium dioxide particles are introduced to the fluidized bed to form a fluid mixture of the particles and gas in the fluidized bed. The particles are reacted with the gas in the fluid mixture to form particles including titanium dioxide and nitrogen. The particles can be disposed along an air flow path in operative communication with a light source for air treatment.

7 Claims, 4 Drawing Sheets

(51) Int. Cl.
- B01D 53/86 (2006.01)
- B01J 8/18 (2006.01)
- B01J 27/24 (2006.01)
- B01J 35/39 (2024.01)
- B01J 35/50 (2024.01)
- B01J 37/02 (2006.01)

(52) U.S. Cl.
CPC .... *B01D 2255/906* (2013.01); *B01D 2258/06* (2013.01)

(56) References Cited

U.S. PATENT DOCUMENTS

| | | | |
|---|---|---|---|
| 5,573,689 | A | 11/1996 | Fukuoka et al. |
| 5,817,280 | A | 10/1998 | Larsen et al. |
| 7,547,418 | B2 | 6/2009 | Johnson et al. |
| 7,615,512 | B2 | 11/2009 | Orth-Gerber et al. |
| 8,791,044 | B2 | 7/2014 | Varma et al. |
| 9,095,636 | B2 | 8/2015 | Schmidt et al. |
| 2002/0169076 | A1 | 11/2002 | Takeshi et al. |
| 2003/0050196 | A1* | 3/2003 | Hirano ............... B01J 21/06 507/238 |
| 2004/0058149 | A1 | 3/2004 | Zhou et al. |
| 2006/0210798 | A1 | 9/2006 | Burda |
| 2007/0248831 | A1 | 10/2007 | Nishihara et al. |
| 2010/0087310 | A1 | 4/2010 | Kisch et al. |
| 2010/0213046 | A1 | 8/2010 | Grimes et al. |
| 2010/0322836 | A1 | 12/2010 | Benham et al. |
| 2011/0123423 | A1 | 5/2011 | Ciambelli et al. |
| 2011/0224066 | A1 | 9/2011 | Schmidt et al. |
| 2011/0266136 | A1 | 11/2011 | Varma et al. |
| 2012/0121470 | A1 | 5/2012 | Morito et al. |
| 2012/0171079 | A1 | 7/2012 | Morito et al. |
| 2019/0336952 | A1 | 11/2019 | Mcgee |

FOREIGN PATENT DOCUMENTS

| | | |
|---|---|---|
| EP | 1908730 A1 | 4/2008 |
| FR | 3011819 A1 | 4/2015 |
| JP | 2005047786 A | 2/2005 |
| WO | 2012052624 A1 | 4/2012 |

OTHER PUBLICATIONS

European Search Report issued for European Application No. 19172141.4 dated Jul. 2, 2019; 15 Pages.

Jo et al.; "Application of Visible-Light Photocatalysis with Nitrogen-Doped or Unmodified Titanium Dioxide for Control of Indoor-Level Volatile Organic Compounds"; Journal of Hazardous Materials 164; 2009; pp. 360-366.

Ruzmanova et al.; "A Novel Approach for the Production of Nitrogen Doped TiO2 Nanoparticles"; Chemical Engineering Transactions; vol. 43; 2015; pp. 721-726.

Samokhvalov; "Hydrogen by Photocatalysis with Nitrogen Codoped Titanium Dioxide"; Renewable and Sustainable Energy Reviews 72; 2017; pp. 981-1000.

Valentin et al.; "N-doped TiO2: Theory and Experiment"; Science Direct—Chemical Physics 339; 2007; pp. 44-56.

Wang et al.; "Nitrogen-Doped Simple and Complex Oxides for Photocatalysis: A Review"; Progress in Material Science 92; 2018; pp. 33-63.

European EPO Official Letter for Application No. 19172141.4, mailed Feb. 16, 2024, 5 pages.

\* cited by examiner

GAS TREATMENT METHOD AND MATERIALS

CROSS-REFERENCE TO RELATED APPLICATIONS

This Application is a division of U.S. application Ser. No. 15/968,691 filed May 1, 2018, the disclosure of which is incorporated herein by reference in its entirety.

BACKGROUND

This disclosure relates to air treatment, and in particular to photocatalytic materials for air treatment.

Conditioned spaces such as building interiors and aircraft cabins can utilize air purification systems to remove airborne substances such as benzene, formaldehyde, and other contaminants from the air supply. Some of these purification systems include photocatalytic reactors that utilize a substrate or cartridge containing a photocatalyst oxide. When placed under an appropriate light source, typically a UV light source, the photocatalyst oxide interacts with airborne water molecules to form hydroxyl radicals or other active species. The hydroxyl radicals react with the contaminants and initiate an oxidation reaction that converts the contaminants into less harmful compounds, such as water and carbon dioxide. It is further believed that the combination of water vapor, suitably energetic photons, and a photocatalyst also generates an active oxygen agent like hydrogen peroxide as suggested by W. Kubo and T. Tatsuma, 20 Analytical Sciences 591-93 (2004). A commonly used UV photocatalyst is titanium dioxide ($TiO_2$), otherwise referred to as titania.

BRIEF DESCRIPTION

An air treatment method is disclosed. According to the method, a gas comprising hydrogen and nitrogen, or comprising hydrogen and ammonia, or comprising hydrogen, nitrogen, and ammonia, is introduced to a fluidized bed. The gas flows through the fluidized bed, and particles comprising titanium dioxide are introduced to the fluidized bed to form a fluid mixture of the particles and gas in the fluidized bed. The particles are reacted with the gas in the fluid mixture to form particles comprising titanium dioxide and nitrogen. The particles comprising titanium dioxide and nitrogen are disposed along an air flow path in operative communication with a light source. The light source is activated and the particles are contacted with air to be treated.

In some embodiments, the air to be treated is onboard an aircraft, and the particles with the air to be treated comprises compressing outside low pressure air and contacting the compressed air with the particles.

In any one or combination of the foregoing embodiments, the method further includes delivering the air that has contacted the particles to a conditioned interior airspace.

A method of making nitrogen-doped titanium dioxide is disclosed. According to the method, a gas comprising hydrogen and nitrogen, or comprising hydrogen and ammonia, or comprising hydrogen, nitrogen, and ammonia, is introduced to a fluidized bed. The gas flows through the fluidized bed and through particles comprising titanium dioxide to form a fluid mixture of the particles and gas in the fluidized bed. The particles are reacted with the gas in the fluid mixture to form particles comprising titanium dioxide and nitrogen.

An air treatment system is disclosed. The air treatment system includes an air source and a catalytic reactor. The catalytic reactor comprises an inlet in operative fluid communication with the air source, an outlet, catalyst particles comprising titanium dioxide and nitrogen made by the above-described method disposed on a fluid flow path between the inlet and the outlet, and a light source in operative communication with the catalyst particles.

A method of making an air treatment device is disclosed. According to the method, a gas comprising hydrogen and nitrogen, or comprising hydrogen and ammonia, or comprising hydrogen, nitrogen, and ammonia, is introduced to a fluidized bed. The gas flows through the fluidized bed, and particles comprising titanium dioxide are introduced to the fluidized bed to form a fluid mixture of the particles and gas in the fluidized bed. The particles are reacted with the gas in the fluid mixture to form particles comprising titanium dioxide and nitrogen. The particles comprising titanium dioxide and nitrogen are disposed along an air flow path in operative communication with a light source.

In any one or combination of the foregoing embodiments, the gas can comprise hydrogen and nitrogen.

In any one or combination of the foregoing embodiments, the gas can comprise hydrogen and ammonia.

In any one or combination of the foregoing embodiments, the gas can comprise hydrogen, nitrogen, and ammonia.

In any one or combination of the foregoing embodiments, the particles can have a diameter of 100 nm to 50 µm.

In any one or combination of the foregoing embodiments, the titanium dioxide can comprise at least 99 wt. % anatase titanium dioxide.

In any one or combination of the foregoing embodiments, the titanium dioxide can comprise anatase and rutile titanium dioxide with an anatase:rutile weight ratio of 90:10 to 10:90.

In any one or combination of the foregoing embodiments, the method can include flowing the gas through the fluidized bed at a velocity of $6 \times 10^{-8}$ m/s to 0.2 m/s.

In any one or combination of the foregoing embodiments, the method can include introducing the gas to an outer chamber of the fluidized bed, flowing the gas to an inner chamber positioned within the outer chamber, and introducing the particles comprising titanium dioxide to the inner chamber to form the fluid mixture of the particles and the gas in the inner chamber.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
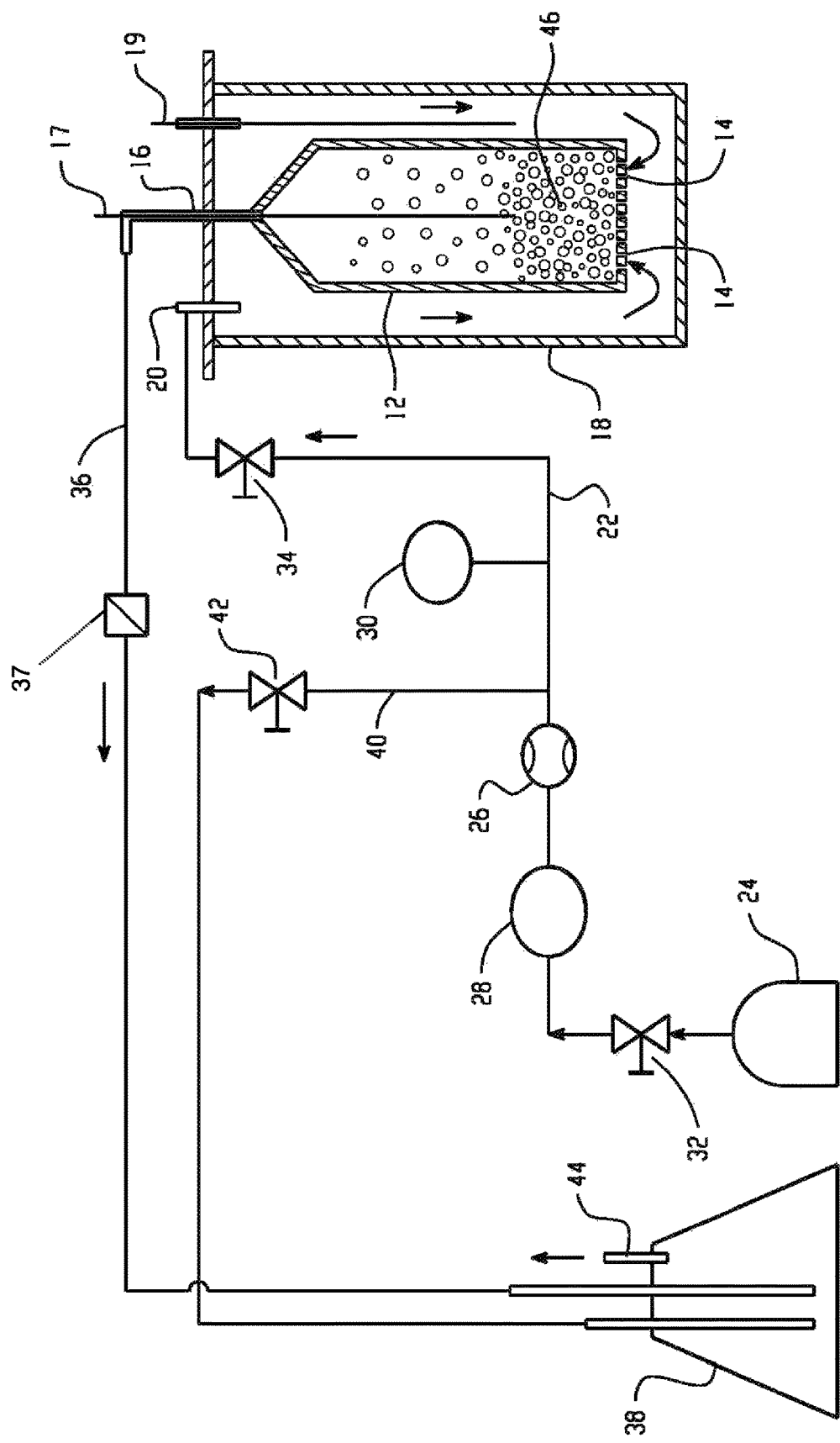
FIG. 1 is a schematic depiction of an example embodiment of a fluidized bed assembly.

An exemplary fluidized bed assembly for treating titanium dioxide particles is shown in FIG. 1. As shown in FIG.

1, the assembly includes a fluidized bed 12 having inlet openings 14 disposed at one end of the fluidized bed 12 and an outlet opening 16 disposed at the opposite end of the fluidized bed 12. The fluidized bed 12 is disposed inside of an outer tubing 18, with outlet 16 extending to the outside of outer tubing 18. During operation, the fluidized bed assembly is disposed in a furnace (not shown) to provide heat. Thermocouples 17 and 19 are disposed to monitor temperature in the fluidized bed 12 and outer tubing 18, respectively. An inlet 20 is connected to a gas feed line 22. A gas source 24 such as a storage tank or a gas-generating reactor is connected to gas feed line 22 to supply a gas feed to the fluidized bed 12. Other components, such as mass flow controller 26, pressure regulating valve 28, pressure sensor 30, and shut-off valves 32 and 34 are also disposed in the gas feed line 22 for monitoring and controlling the flow rate and pressure of the gas delivered to the fluidized bed 12. Fluidized bed outlet 16 is connected to outlet line 36 that includes a check valve 37, and is connected to a water or other liquid bubbler 38. A bleed line 40 with shut-off valve 42 also connects feed line 22 to the bubbler 38, which is vented to atmosphere through exhaust port 44.

In operation, a gas mixture comprising nitrogen and hydrogen, or a gas comprising ammonia and hydrogen, or a gas comprising nitrogen, hydrogen, and ammonia, or a gas of pure ammonia or consisting essentially of ammonia, from gas source(s) 24 is fed through feed line 22, with the flow rate and gas pressure controlled by mass flow controller 26 and pressure regulating valve 28. In some embodiments, the gas comprises an amount of hydrogen in a range having a low end of 5 mol %, or 10 mol %, or 30 mol %, or 40 mol %, or 60 mol %, and an upper end of 90 mol %, or 80 mol %, or 85 mol %, or 90 mol %, or 95 mol %, based on the total mole percentage of nitrogen, hydrogen, and/or ammonia, in the gas. This approach can also be taken with $NH_3/H_2$ mixtures which can also be used in controlled nitriding processes. Therefore, this technique can be applied with $NH_3$ concentrations ranging from 5-95% and respective $H_2$ concentrations between 95 and 5%. The above upper and lower range endpoints can be independently combined to disclose a variety of different ranges, and each possible combination of endpoints to form a range is hereby expressly disclosed. Other gases (e.g., helium, argon) can be included as well, and the gas can in some embodiments comprise an amount of nitrogen in a range having a low end of 5 mol %, or 10 mol %, or 15 mol %, or 20 mol %, and an upper end of 40 mol %, or 60 mol %, or 70 mol %, based on the total moles of gas. The above upper and lower range endpoints can be independently combined to disclose a variety of different ranges, and each possible combination of endpoints to form a range is hereby expressly disclosed. The nitrogen- and hydrogen-containing gas enters the furnace 18 through inlet 20. The gas can be heated, for example, as it passes through the space between fluidized bed 12 and outer tubing 18 to enter the fluidized bed 12 through inlet 14. The fluidized bed 12 has $TiO_2$ particles 46 disposed therein, and the upward gas flow rate through the fluidized bed applies sufficient upward force to the particles 46 to counteract the force of gravity acting on the particles so that they are suspended in a fluid configuration in the fluidized bed space. The gas flow is generally maintained below levels that would carry entrained particles out of the fluidized bed through outlet 16, and outlet 16 can also be fitted with a filter or screen to further assist in keeping metal powder particles 46 from exiting the fluidized bed 12. Nitrogen-containing gas exits the fluidized bed 12 through outlet 16 and flows via outlet line 36 to the bubbler 38, from which it is exhausted to the atmosphere through exhaust port 44.

In some embodiments, treatment of the $TiO_2$ particles is continued for a duration and/or under conditions to provide a target nitrogen content integrated into the atomic lattice structure of the metal oxide of the particles. Although the disclosure is not bound by any particular theory or mode of operation, it is believed that a target nitrogen content can provide enhanced photocatalytic activity. In some embodiments, treatment of the particles in the fluidized bed imparts a nitrogen content to the particles in a range having a lower limit of 0.25 at. %, 1.25 at. %, or 5 at. %, and an upper limit of 10 at. %, 25 at. %, or 50 at. %. These range limits can be independently combined to form different ranges, and each range represented by a possible combination of the above range limits is hereby expressly disclosed. In some embodiments, the reaction temperature in the fluidized bed 12 can be in a range having a lower limit of 200° C., 300° C., or 500° C., and an upper limit of 600° C., 700° C., or 800° C. These range limits can be independently combined to form different ranges, and each range represented by a possible combination of the above range limits is hereby expressly disclosed. The gas can flow at a velocity sufficient to create a fluid mixture with the particles. In some embodiments, the gas can flow through the fluidized bed at a velocity of $6 \times 10^{-8}$ m/s (meters per second) (e.g., 0.003 ml/min for 1" OD reactor) to 0.2 m/s (e.g., 3745 ml/min for 1" OD reactor). The $TiO_2$ particles can be treated in the fluidized bed for periods (i.e., contact time with the nitrogen-containing gas) for a duration in a range having a lower limit of 0.50 hours, 1.00 hours, or 3.00 hours, and an upper limit of 5.00 hours, 10.00 hours, or 20.00 hours. These range limits can be independently combined to form different ranges, and each range represented by a possible combination of the above range limits is hereby expressly disclosed. In batch mode, such as depicted in the treatment scheme shown in FIG. 1, the fluidized bed is operated for the specified amount of time to achieve the desired contact time. In a continuous mode, throughput of the particles through the fluidized bed can be adjusted to achieve an average residence time equal to the desired contact time.

The particle size of the $TiO_2$ particles can vary depending on factors such as the desired final particle size, fluidized bed parameters such as velocity of gas flow in the fluidized bed, etc. In some embodiments, particle size is in a range having a lower limit of 100 nm, 300 nm, or 700 nm, and an upper limit of 0.25 µm, 10 µm, or 50 µm. These range limits can be independently combined to form different ranges, and each range represented by a possible combination of the above range limits is hereby expressly disclosed. In some embodiments, the $TiO_2$ can be in anatase form, e.g., ≥99 wt. % anatase form. In some embodiments, the $TiO_2$ can be in a mixed anatase/rutile form, e.g., with an anatase:rutile weight ratio of 99:1 to 1:99.

In some embodiments, the fluidized bed can provide various technical benefits (e.g., compared to the fixed beds that are conventionally used with ammonia to make metal nitrides such as vanadium nitride), including but not limited to providing uniform reaction conditions for the population of $TiO_2$ particles, avoiding localized hot spots that can occur in fixed beds. The gas mixture can comprise hydrogen and nitrogen, or ammonia, or a mixture of hydrogen, nitrogen, and ammonia. The use of a gas mixture comprising nitrogen and hydrogen can in some embodiments help to avoid heat transfer problems associated with the endothermic decomposition of ammonia, and also allow for recycling of essentially all of the gas fed to the fluidized bed. In some embodiments, the gas fed to the fluidized bed is free of ammonia. In some embodiments, the gas mixture comprises nitrogen and hydrogen, and also comprises ammonia in an amount less than or equal to 5 mol %. In some embodiments, the gas mixture comprises nitrogen and hydrogen, and also comprises ammonia in an amount less than or equal to 10 mol %. In some embodiments, the gas mixture comprises nitrogen and hydrogen, and also comprises ammonia in an amount of from 5 mol % to less than 100 mol % ammonia. In some embodiments, the gas mixture comprises ammonia without a nitrogen/hydrogen mixture.

After emergence from the fluidized bed, the $TiO_2$ particles 46 can in some embodiments be subjected to further processing before integration into an air treatment device. For example, in some embodiments, the $TiO_2$ powder can be separated into different particle size ranges that can be targeted toward different applications.

Figure 2:
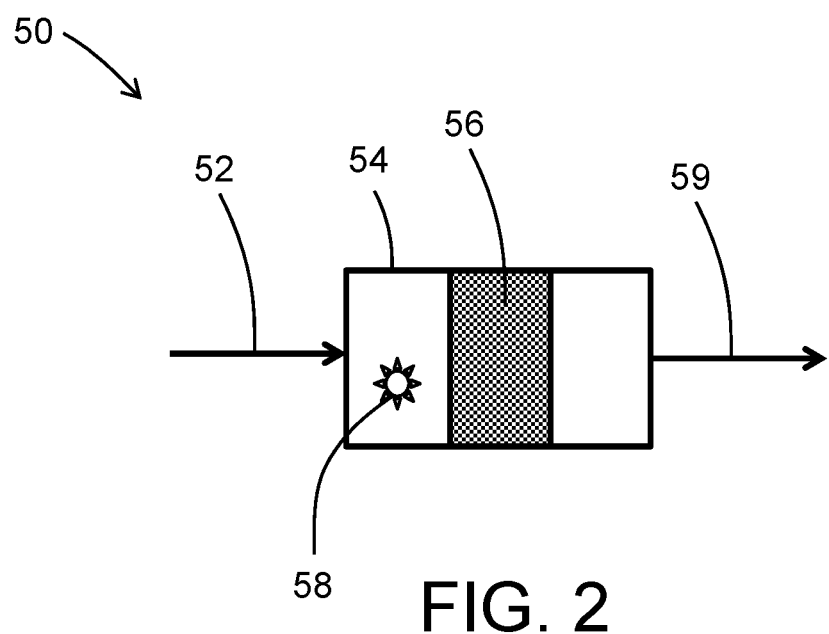
FIG. 2 is a schematic depiction of an example embodiment of a gas treatment system.

With reference now to FIG. 2, the Figure schematically depicts an example embodiment of a gas treatment system 50. As shown in FIG. 2, a gas 52 to be treated is introduced to a photocatalytic treatment module 54. The photocatalytic module 54 includes photocatalytic $TiO_2$ particles 46 taken from the fluidized bed 12 (FIG. 1). The $TiO_2$ particles can be disposed on a substrate such as a porous substrate, for example a carbon or ceramic substrate. Various substrate configurations can be utilized such as a honeycomb, corrugated sheet, fiber or other monolith structure. Ceramics for substrates can include but are not limited to sillimanite, petalite, cordierite, mullite, Zircon, Zircon mullite, spodumene, alumina, or alumina-titanate. The photocatalytic particles can be deposited onto the substrate by dispersing in a fluid medium and applying to the substrate. Application techniques can include, but are not limited to, wash-coating, dip-coating, spraying, rolling, brushing, and other manual or automated application techniques. A light source such as a UV light source 56 is directed onto the photocatalytic $TiO_2$ particles 46 to induce photocatalytic formation of reactive species, for example formation of hydroxyl ions from water molecules in the gas 52, that can react with other species in the gas 52 such as organic contaminants. Treated gas 58 exits from an outlet of the photocatalytic treatment module 54.

Figure 3A:
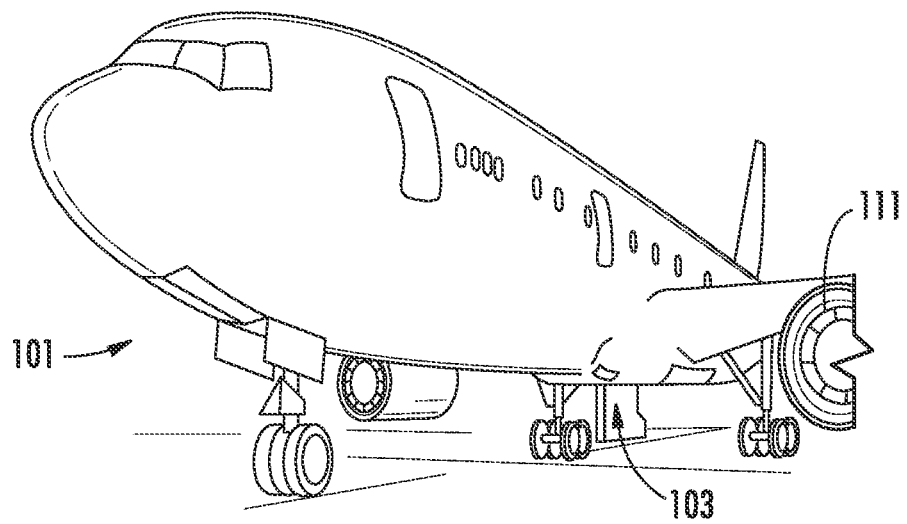
FIG. 3A is a schematic illustration of an aircraft that can incorporate various embodiments of the present disclosure.
Figure 3B:
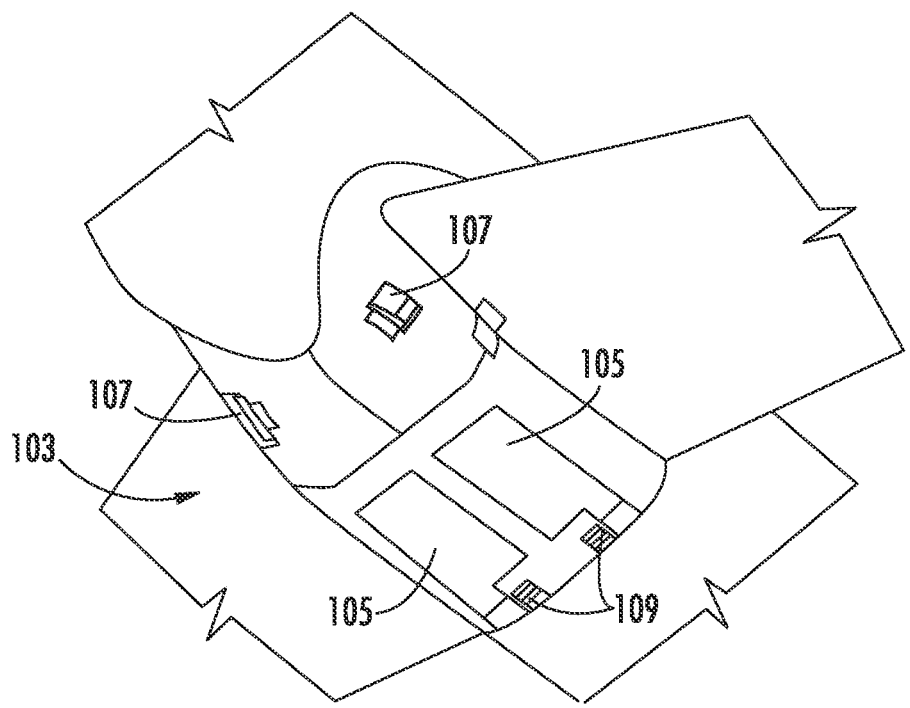
FIG. 3B is a schematic illustration of a bay section of the aircraft of FIG. 3A.

A notable application for photocatalytic treatment of cabin air onboard pressurized aircraft. As shown in FIGS. 3A-3B, an aircraft can include an aircraft body 101, which can include one or more bays 103 beneath a center wing box. The bay 103 can contain and/or support one or more components of the aircraft 101. For example, in some configurations, the aircraft can include environmental control systems and/or fuel inerting systems within the bay 103. As shown in FIG. 1B, the bay 103 includes bay doors 105 that enable installation and access to one or more components (e.g., environmental control systems, fuel inerting systems, etc.). During operation of environmental control systems and/or fuel inerting systems of the aircraft, air that is external to the aircraft can flow into one or more ram air inlets 107. The outside air may then be directed to various system components (e.g., environmental conditioning system (ECS) heat exchangers) within the aircraft. Some air may be exhausted through one or more ram air exhaust outlets 109. Also shown in FIG. 3A, the aircraft includes one or more engines 111. The engines 111 are typically mounted on wings of the aircraft and are connected to fuel tanks (not shown) in the wings, but may be located at other locations depending on the specific aircraft configuration. In some aircraft configurations, air can be bled from the engines 111 and supplied to environmental control systems and/or fuel inerting systems, as will be appreciated by those of skill in the art.

Figure 4:
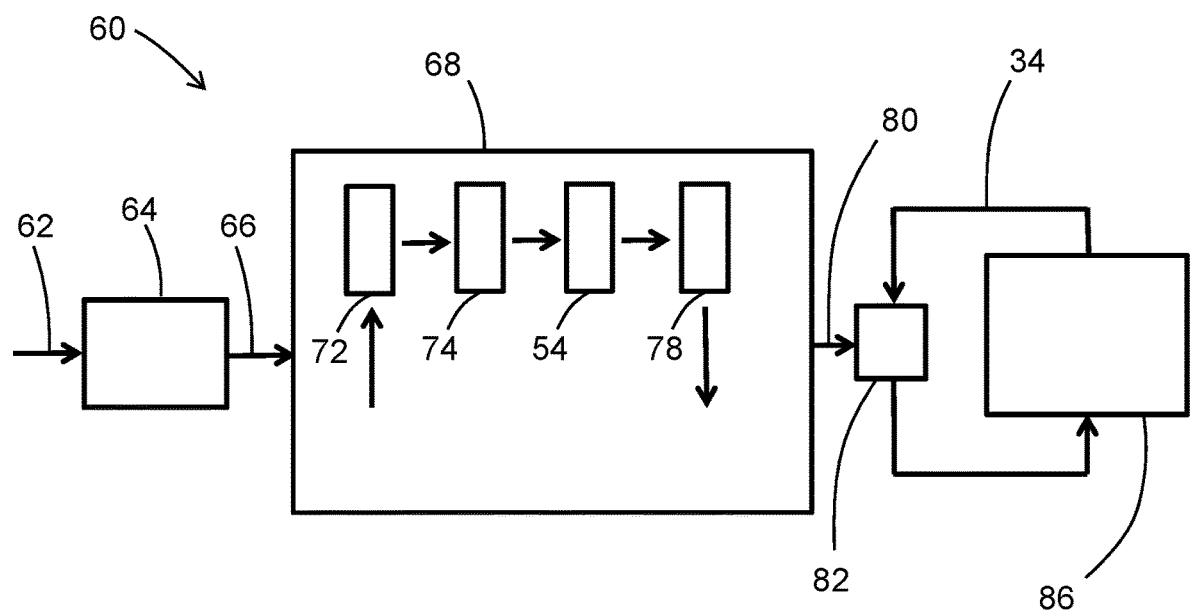
FIG. 4 is a schematic depiction of an example embodiment of an aircraft air treatment system.

An example embodiment of an aircraft cabin air ozone removal system is schematically depicted in FIG. 4. As shown in FIG. 4, aircraft cabin air system 60 receives outside ambient air 62 and directs it to a compressor 64. The compressor 64 can be a compressor section of a turbo-compressor aircraft engine, or can be an electrically-powered compressor. The compressor 64 compresses the air to a pressure of at least 15 psia, and typically to a greater pressure, which is then reduced by an aircraft environmental control system (ECS) pack 68. In some embodiments, a turbo-compressor aircraft engine can provide bleed flow at 40-60 psi, whereas an electrically-powered compressor on a bleed-less or low-bleed aircraft architecture may provide compressed air at lower pressures (e.g., about 20 psi). The compressor 64 produces compressed air 66, which is directed to the ECS pack 68. As depicted in the example embodiment of FIG. 3, the ECS pack 68 includes multiple modules in addition to the photocatalytic module 54, any of which can optionally be used individually in combination with the photocatalytic module 54 or can be combined in groups with the photocatalytic module 54. As shown in FIG. 4, the air 66 enters a filter module 72 such as a HEPA (high efficiency particulate absorber) filter, and is directed to a VOC (volatile organic content) absorber 74 such as an activated carbon filter that can adsorb VOC carbon and later discharge it during regeneration, and then to the photocatalytic module 54. Lastly, the air flow is directed through an ozone removal module 78, such as a noble metal catalytic module. Noble metal catalysts for the removal of ozone can include a metal selected from ruthenium, rhodium, palladium, iridium, platinum, gold, or combinations comprising any of the foregoing. In some embodiments, the noble metal is selected from palladium or platinum and their alloys. Noble metal catalysts can provide significant catalytic activity in the temperature range of 50-350° C., and in some embodiments the noble metal catalyst is disposed in an airflow path in that temperature range.

The ECS pack can also include other customary components for air cycle cooling systems, including heat exchangers, compressors (e.g., turbine-blade compressors), turbines, and heat exchanger/water removal units. Air cycle cooling systems can be based on three-wheel architecture (a fan, a compressor, and a turbine) or four-wheel architecture (a fan, a compressor, and two turbines). In some embodiments, the ECS pack cools bleed air in a ram air heat exchanger, partially re-compresses it in a turbine-powered compressor, cools the partially re-compressed air in a second pass through the ram air heat exchanger, expands and further cools the air flow and removes water with a turbine in a flow loop with a heat exchanger water removal unit, and, in the case of a four-wheel architecture further expands and cools the air in a second turbine. The location of the photocatalytic module 54 and the other modules in flow paths through the ECS pack can vary depending on the system operating parameters of the ECS pack, and the temperature and other environmental requirements for effective adsorptive and catalytic effect. FIG. 3 depicts an example embodiment, and modifications are contemplated. For example, the modules shown in FIG. 3 do not have to be disposed in the order shown in FIG. 3, and can instead be disposed in different orders with respect to the direction of air flow. Also, the modules do not have to be lined up consecutively, but can instead be disposed at different paths along the air cycle process flow, with other ECS components disposed along the air flow path between any or all of the modules shown in FIG. 3.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

What is claimed is:

1. A system for making nitrogen-doped titanium dioxide, comprising:
    a gas source comprising hydrogen and ammonia, or comprising hydrogen, nitrogen, and ammonia;
    a source of titanium dioxide particles;
    a fluidized bed arranged to receive gas from the gas source and titanium dioxide particles from the source of titanium dioxide particles and form a fluid mixture of the particles in the gas, wherein the fluidized bed causes 5 atomic percent to 50 atomic percent nitrogen to be integrated into an atomic lattice structure of the titanium dioxide.

2. The system of claim 1, wherein the gas comprises hydrogen and ammonia.

3. The system of claim 1, wherein the gas comprises hydrogen, nitrogen, and ammonia.

4. The system of claim 1, wherein the titanium dioxide comprises at least 99 wt. % anatase titanium dioxide.

5. The system of claim 1, wherein the particles have a diameter of 100 nm to 50 μm.

6. A method of making nitrogen-doped titanium dioxide, comprising:
    introducing a gas comprising hydrogen and ammonia, or comprising hydrogen, nitrogen, and ammonia to a fluidized bed;
    flowing the gas through the fluidized bed, and through particles comprising titanium dioxide in the fluidized bed to form a fluid mixture of the particles and the gas in the fluidized bed; and
    reacting the particles with the gas to form particles comprising titanium dioxide and nitrogen, wherein 5 atomic percent to 50 atomic percent nitrogen is integrated into an atomic lattice structure of the titanium dioxide.

7. A method of making an air treatment device, comprising:
    making particles comprising titanium dioxide and nitrogen according to the method of claim 6; and
    disposing the particles along an air flow path in operative communication with a light source.

* * * * *